United States Patent [19]

Nissenkorn

[11] Patent Number: 4,973,301

[45] Date of Patent: Nov. 27, 1990

[54] CATHETER AND METHOD OF USING SAME

[76] Inventor: Israel Nissenkorn, 11 Barazani Street, Ramat-Aviv, Tel Aviv, Israel

[21] Appl. No.: 378,153

[22] Filed: Jul. 11, 1989

[51] Int. Cl.$^5$ ............................................. A61M 36/00
[52] U.S. Cl. ....................................... 604/08; 604/54; 604/93
[58] Field of Search ................. 604/8, 21, 54, 93, 164, 604/165, 170, 280, 281, 264

[56] References Cited

U.S. PATENT DOCUMENTS

| | | | |
|---|---|---|---|
| 3,938,529 | 2/1976 | Gibbons | 604/8 |
| 3,995,642 | 12/1976 | Adair | 604/8 |
| 4,790,810 | 12/1988 | Pugh, Jr. et al. | 604/8 |
| 4,813,925 | 3/1989 | Anderson, Jr. et al. | 604/8 |
| 4,820,262 | 4/1989 | Finney | 604/8 |

Primary Examiner—John D. Yasko
Attorney, Agent, or Firm—Merchant, Gould, Smith, Edell Welter & Schmidt

[57] ABSTRACT

A self-retaining intraurethral catheter (IUC) for indwelling implantation made of semi-rigid plastic material comprising a central tubular portion and integrally formed therewith proximal and distal crowns having larger diameters than the tubular portion, said crowns having apertures communicating with the bore of said tubular portion, wherein said proximal crown is adapted to be retained in the bladder neck and said distal crown adapted to engage the prostatic urethra and prevent proximal displacement of the IUC in the urethra; an applicator set and method for using same.

12 Claims, 2 Drawing Sheets

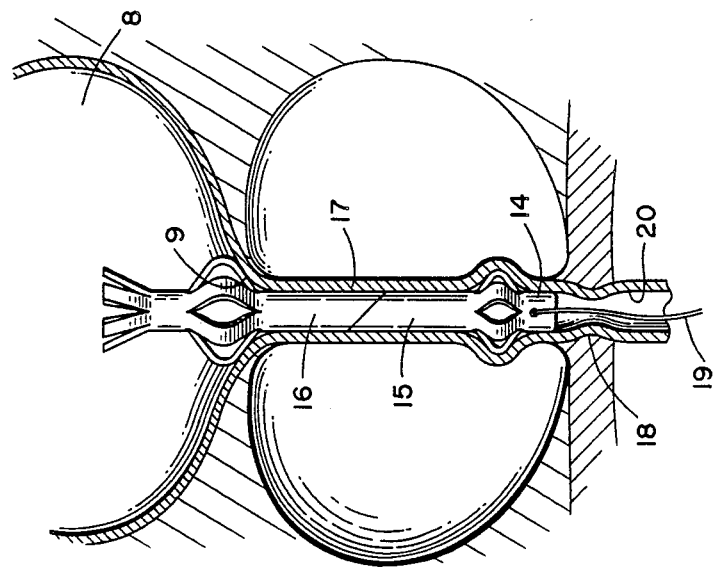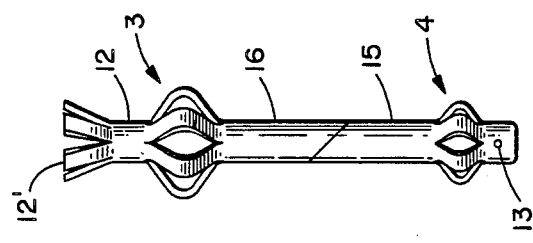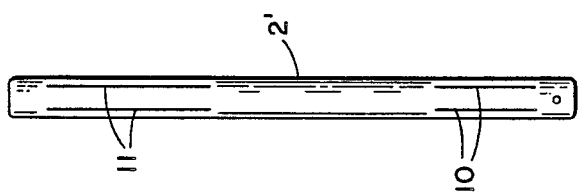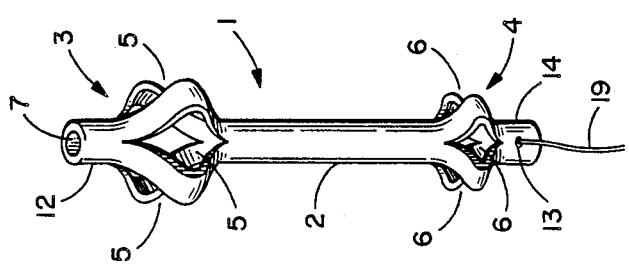

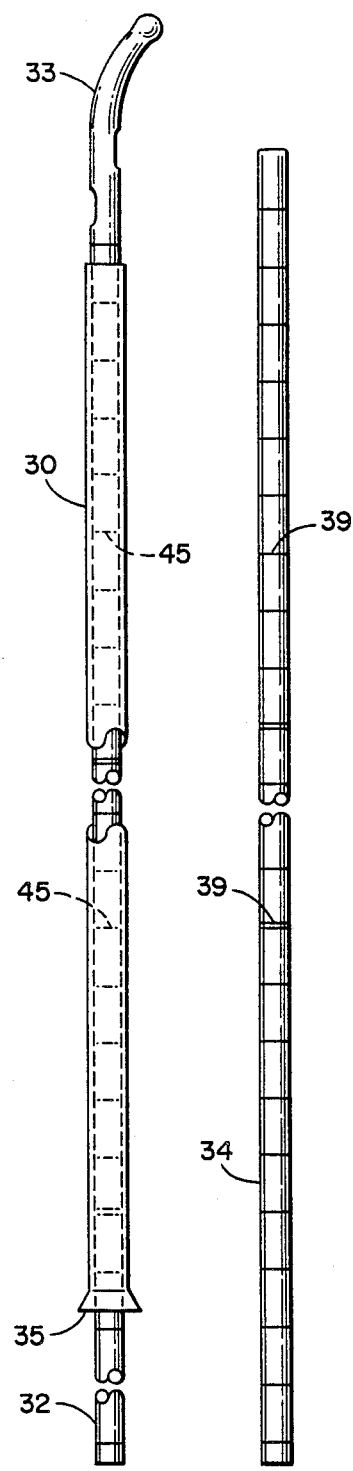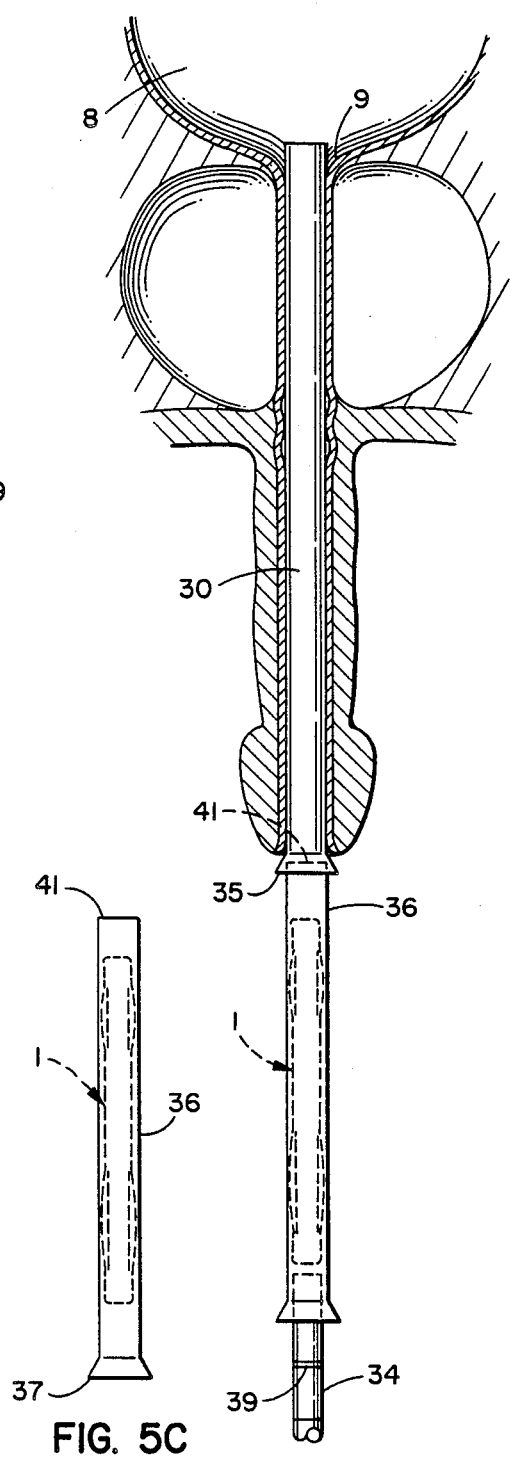
FIG. 5A  FIG. 5B  FIG. 5C  FIG. 6

4,973,301

CATHETER AND METHOD OF USING SAME

FIELD OF THE INVENTION

The present invention relates to a novel self-retaining intraurethral catheter (IUC), an applicator set and method for using same. This new device may be used as an alternative to an indwelling catheter in patients with urinary retention caused by infravesical obstruction and may be an alternative to prostatectomy in patients who are at high risk for surgery.

BACKGROUND OF THE INVENTION

Urethral catheters have generally been used for four purposes: to relieve urinary retention, to test residual urine, to obtain urine directly from the bladder for diagnostic purposes, and for bladder lavage, instillations or other therapeutic reasons.

Out of the four purposes listed above, catheters are no longer needed for testing residual urine, nor to obtain urine directly from the bladder.

The use of a cathether for therapeutic purposes, such as bladder instillation, is essential, but in such cases a catheter is introduced for a short period of time and is removed shortly after it has been inserted, so the patient suffers relatively little discomfort. The same may be said for the use of a catheter after bladder or prostatic surgery.

The main reason for which catheters are left indwelling for weeks or months is for relief of urinary retention, most often because of infravesical prostatic obstruction.

In many instances an indwelling catheter has to be left for an extended period of time because the patient is not fit for surgery, or the condition of the patient requires that surgery should be postponed. Unfortunately, there is often a waiting list of patients for prostatectomy, many of whom must endure an indwelling catheter for weeks or even months.

An indwelling catheter is not only a common cause of urinary tract infection, urethral inflammation and discharge, possible urethral strictures and many other complications, but is also a serious psychological problem. Most men with an indwelling catheter feel they lose dignity, are unable to perform sexually, and are often unable to continue their routine life. They have to suffer all this in addition to the local discomfort caused by the catheter irritating the entire length of the urethra, in spite of the fact that only a short length of a few centimeters is needed to overcome the obstruction.

Only one alternative for an indwelling urethral catheter has been tried till now. This is an iron, gold-coated spiral known as PROSTAKAT (TM).

The intraurethral catheter of the present invention is a simpler and more physiological prosthesis and is easier to insert into the prostatic urethra, easier to remove, and much more economical in comparison to the gold-coated spiral.

A catheter for use in internal biliary drainage, known as the Miller double mushroom biliary stent, is also known wherein a double mushroom design helps maintain the stent position. These Miller stents come in diameter sizes of 10.0, 12.0 and 14.0 French.

SUMMARY OF THE INVENTION

It is the object of this invention to provide an indwelling self-retaining relatively short length intraurethral catheter (IUC) for relief of urinary retention.

It is a further object of this invention to provide self-retaining relatively short length IUC for indwelling over a prolonged period of time which enables satisfactory voiding without developing urinary tract infection.

A still further object of this invention is to provide an applicator set specially designed for inserting the novel intraurethral catheter.

Another object of this invention is to provide a method for inserting an intraurethral catheter for relieving urinary retention.

In accordance with this invention, there is thus provided a self-retaining IUC for indwelling implantation made of semi-rigid plastic material comprising a central tubular portion having a diameter of from 16–20 French, proximal and distal crowns of larger diameter integrally formed with said tubular portion, said crowns having apertures communicating with the hollow of said tubing, said proximal crown adapted to be retained just above the neck of the bladder and said distal crown adapted to prevent proximal displacement of the IUC in the urethra.

There is also provided according to this invention an applicator set for introducing the novel IUC into the bladder neck and prostatic urethra. This set comprises a tubular sheath, a tubular IUC holder, a Tiemann-type cathether guide and an obturator, said IUC holder having the same diameter as the sheath, said catheter guide and obturator being slidable in said sheath, wherein said guide is adapted to guide and assist positioning the sheath in the urethra, said obturator is adapted to push the IUC out of its holder into the sheath and further until the IUC is properly positioned in the bladder neck and prostatic urethra.

BRIEF DESCRIPTION OF THE DRAWINGS

FIG. 1 illustrates one embodiment of an IUC of this invention;

FIG. 2 shows a precursor of the IUC of FIG. 1 before final completion of manufacture;

FIG. 3 illustrates another IUC embodiment of the invention;

FIG. 4 schematically illustrates an indwelling IUC in accordance with the invention;

FIGS. 5a–c illustrate the applicator set of the invention; and

FIG. 6 schematically illustrates the method of inserting an IUC of the invention.

Referring now to FIG. 1, this illustrates an IUC generally designated 1 which comprises a central tubular portion 2 with integral proximal 3 and distal 4 crowns. The crowns 3 and 4 have apertures 5 and 6 respectively which allow fluid to flow therethrough into the hollow inner tube 7 of the IUC. The IU of this invention is constructed of semi-rigid plastic, preferably radiopaque polyurethane such as Puroflex-Urosoft (TM). It will be noted that the proximal crown 3 is larger than the distal crown 4. This is because these two crowns serve different purposes. Thus the proximal crown 3 is intended to sit within the bladder 8 (FIG. 4) and rest freely in the bladder neck 9 preventing distal displacement of the IUC 1. The distal crown 4 on the other hand presses against the prostatic urethral inner wall 17 and prevents proximal displacement of the IUC. A hole 13 is provided at the distal end of the IUC for engaging a suture or filament 19 for easier removal of the IUC from the urethra by merely pulling at it.

The indwelling IUC of this invention can range in diameter from about 16 to 20 French. Its length will depend on the individual in whom it is to be inserted, based on the urethral length between the bladder neck and external sphincter, but usually the lengths range from 4 cm to 8 cm, preferably from 5 cm to 7.5 cm. It is important that the length of the IUC be such that the crown 3 sits in the bladder neck 9 and that its distal end 14 be about 1 cm-1.5 cm above the veru montanum.

The IUC 1 can be readily manufactured by taking suitable tubing 2' (see FIG. 2) and providing appropriate slits 10 and 11 which upon compression and heat setting of the tube 2' form distal 4 and proximal 3 crowns respectively.

FIG. 3 illustrates another type of IUC within the scope of the invention wherein the proximal tube ending 12 which is intended to sit inside the bladder is also slit 12' to provide additional passage for urine to flow from the bladder into the IUC thereby minimizing opportunity for blockage at this end.

The IUC of this invention may also be manufactured by using two different semi-rigid plastics each having a different degree of flexibility. Thus for example (with refrerence to FIG. 3) the distal portion 15 of the IUC 1 can be made of a more flexible polyurethane than the proximal section 16, thereby further reducing the friction between the IUC and urethra and minimizing even more the chances for irritation or infection.

The applicator set shown in FIGS. 5a-c comprises the following items: a hollow guide sheath 30 (FIG. 5a) about 15 cm-20 cm long and about 22 French in diameter preferably made of teflon, said tube having one flared end 35; a Tiemann-type catheter guide 32 having a curved head 33 and which is preferably graduated 45 with equidistant lines about 1 cm apart; an obturator 34 comprising preferably a teflon rod preferably being similarly graduated 39; and an IUC holder 36 consisting of a shorter version of the guide tube 30 also having a flared end 37.

One method for introducing the IUC of this invention is as follows with reference to FIG. 4.

The patient is placed in a lithotomy position with a regular indwelling catheter, through which 150 ml of a saline is infused into the bladder, the catheter is then removed, and the urethra is lubricated with 10 ml of lidocaine jelly. A penile clamp, obstructing the distal urethra, is left for 10 minutes. The catheter is then removed and the cystoscope sheath containing the IUC in its curved end is introduced into the bladder (the previously infused saline begins to flow out from the cystoscope). The cystoscope is drawn slightly into the bladder neck when the fluid has ceased to flow out of the cystoscope sheath, the IUC is then expelled by the obturator of the cystoscope. The cystoscope sheath, together with the obturator is removed from the urethra. The length of the prostatic urethra should be measured endoscopically or by ultrasound, in order that the appropriate length IUC may be chosen and inserted. To this end consideration should be given to the fact that the distal end (see FIG. 4) of the IUC should not interfere with the distal continuance mechanism. Therefore the distal end 14 of the IUC should be distal to the veru montanum 18, about 1-1.5 cm.

A non-resorbable multifilament nylon/silk 0.20 mm suture 19, connected to the distal end 14 of the IUC 1 remains in the urethra 20, emerging from it. If necessary, the intraurethral catthether may be removed easily by pulling the thread, after the urethra has been lubricated by lidocaine jelly. If the patient is able to void freely and is continent, the thread may be cut and shortened so that it is left in the navicular part of the urethra. If needed, the nylon/silk suture may be grasped by biopsy forceps and the IUC removed after lubrication of the urethra.

Antibiotic therapy according to the urine culture should be started 24 hours before insertion of the IUC and continued for 5 to 7 days. The patients are followed closely and questioned twice weekly regarding frequency and urgency of micturition, and continence during day and night.

Urine cultures are taken weekly and ultrasounds (for measuring residual urine) are performed twice every week for the first two weeks. Fourteen patients were thus treated. In 6 patients, cystourethrograms were done 5 to 7 days after insertion of the IUC. Uroflows were obtained in 11 patients.

An improved method for introducing the IUC is by using applicator set as in FIGS. 5a-c. In this method (see FIGS. 4 & 6) the teflon sheath 30 with guide catheter 32 is introduced into the bladder 8 with the help of the guide head 33. The distance between the bladder neck 9 and the distal end of the urethra can be simply measured by means of the graduations 37 on the catheter guide 32. The catheter guide 32 is removed from the sheath 30 and an IUC holder 36 containing an IUC 1 is fitted onto the sheath 30 so that its tip 41 fits into the flared portion 35 of the sheath 30. The IUC is then expelled by the obturator 34 from the holder 36 into the sheath 30 and therethrough into the bladder neck 9. The distance the IUC moved can be measured by checking the graduations 39 on the obturator 34. The sheath 30 and obturator 34 are then removed from the bladder neck 9 leaving the IUC 1 placed with proximal crown 3 in the bladder neck 9 and distal crown 4 in the prostatic urethra 17. The position of the IUC is verified by urethroscopy.

Intraurethral catheters as in FIG. 1 were inserted in a non-consecutive series of the 14 patients with indwelling catheters (in place from 3 weeks to 18 months) for urinary retention due to benign prostatic hyperplasia. The age of the patients ranged from 54 to 78 years.

The IUC's inserted were 45 mm long in 8 patients and 55 mm long in the other 6 patients. All patients were able to void after insertion of the IUC and were continent. In 11 patients the intraurethral catheter was left in place for 2 to 18 weeks.

In two patients the IUC was removed after 2 and 3 days, because of severe frequency, poor stream and residual urine (of 250 to 320 ml). In the third patient the IUC was removed 6 hours after insertion because of clott retention.

The main complaint of the 11 patients who had sustained the IUC for weeks, was frequency of micturition with voiding intervals of 1.5 hours to 3.5 hours. Some discomfort during voiding (burning sensation and urgency) disappeared 24 to 48 hours after the IUC had been inserted. Three patients had nocturia 3 to 4 times, while 8 patients voided once or twice during the night. None of the patients developed any clinically evident urinary tract infection, including the patient who had the IUC for 18 weeks. All urine cultures were negative. Bacteriuria was found in 3 patients by the end of one week. Voiding cystourethrograms or ultrasounds performed in the patients showed satisfactory voiding with no residue. On mictiography, performed in 11 patients, the maximum flow rates were 8.5 ml/s to 12.5 ml/s (mean 10 ml/s).

I claim:

1. A self-retaining intraurethral catheter (IUC) for indwelling implantation made of semi-rigid plastic material comprising a central tubular portion and integrally formed therewith proximal and distal crowns having larger diameters than the tubular portion, said crowns having apertures communicating with the bore of said tubular portion, wherein said proximal crown is adapted to be retained in the bladder neck and said distal crown adapted to engage the prostatic urethra and prevent proximal displacement of the IUC in the urethra.

2. An intraurethral catheter as in claim 1, wherein the tubular section has a diameter ranging from 16 to 20 French.

3. An IUC as in claim 1, wherein the proximal crown has a larger diameter than the distal crown.

4. An IUC as in claim 1, further comprising a hole near the distal end of the tubing for engaging a suture or filament.

5. An IUC as in claim 1, comprising additional apertures proximal of the proximal crown.

6. An IUC as in claim 1 ranging in length from 4.0 cm to 8.0 cm and preferably from 5.5 cm to 6.5 cm.

7. An IUC as in claim 1 having a distal portion thereof made of a more flexible plastic material than the proximal portion.

8. An applicator set for inserting an IUC into the bladder neck and prostatic urethra consisting of a sheath, a guide, an IUC holder and an obturator wherein said sheath has a flared distal end, is about 15 cm–20 cm long and 22 French in diameter and preferably fabricated from teflon, said guide of the Tiemann catheter type having a curved head, said IUC holder being a shorter version of said sheath, wherein said guide is adapted to help introduce said sheath into the bladder neck, said obturator adapted to expel an IUC housed in said IUC holder through the sheath into the bladder neck.

9. An applicator set as in claim 8 wherein said guide and obturator are about 18 French in diameter.

10. An applicator set as in claim 8 wherein said guide and obturator have graduated markings.

11. A method of introducing an IUC of claim 1 with applicator set consisting of a sheath, a guide, an IUC holder and an obturator wherein said sheath has a flared distal end, is about 15 cm–20 cm long and 22 French in diameter, said guide of the Tiemann catheter type having a curved head, said IUC holder being a shorter version of said sheath, comprising the steps of
   (a) introducing the said sheath with guide therein into the bladder neck;
   (b) removing said guide from said sheath;
   (c) aligning an IUC holder containing an IUC in back of said sheath;
   (d) expelling the IUC with the obturator from the holder through the sheath into the bladder neck; and
   (e) removing sheath and obturator from the urethra leaving the IUC in desired position.

12. A method of implanting an IUC of claim 1 comprising the steps of measuring the length of the prostaic urethra, selecting the proper length IUC so that upon insertion into the urethra its proximal crown will sit in the neck of the bladder and its distal end will be proximal to the veru montanum, and inserting said IUC into the urethra.

* * * * *